United States Patent [19]
Guillaume et al.

[11] Patent Number: 4,993,269
[45] Date of Patent: Feb. 19, 1991

[54] VARIABLE ORIFICE FLOW SENSING APPARATUS

[75] Inventors: Darrell W. Guillaume, Corona; Michael G. Norton, Riverside; Douglas F. DeVries, Redland, all of Calif.

[73] Assignee: Bird Products Corporation, Riverside, Calif.

[21] Appl. No.: 285,086

[22] Filed: Dec. 16, 1988

[51] Int. Cl.⁵ .............................. G01F 1/22
[52] U.S. Cl. ................................. 73/861.53
[58] Field of Search .......... 73/861.52, 861.53, 861.74, 73/861.76; 138/43, 45, 46

[56] References Cited

U.S. PATENT DOCUMENTS

| | | |
|---|---|---|
| 2,892,348 | 6/1959 | Ekstrom, Jr. .................... 73/861.76 |
| 3,403,556 | 10/1968 | Koester . |
| 3,759,099 | 9/1973 | McGregor . |
| 3,795,145 | 3/1974 | Miller . |
| 3,906,792 | 9/1975 | Miller . |
| 3,910,112 | 10/1975 | Gerlach . |
| 3,964,310 | 6/1976 | Stenberg . |
| 4,083,245 | 4/1978 | Osborn ............................ 73/861.53 |
| 4,112,757 | 9/1978 | Hayward . |
| 4,193,301 | 3/1980 | Ferrentino . |
| 4,235,105 | 11/1980 | Walters . |
| 4,304,136 | 12/1981 | McCabe et al. . |
| 4,350,050 | 9/1982 | Nelson . |
| 4,368,646 | 1/1983 | Rogg . |
| 4,474,068 | 10/1984 | Knetsch et al. . |
| 4,552,027 | 11/1985 | Larner . |
| 4,604,902 | 8/1986 | Sabin et al. . |
| 4,614,122 | 9/1986 | Graves ............................ 73/861.74 |
| 4,619,139 | 10/1986 | Rosaen . |
| 4,688,433 | 8/1987 | Silverwater .................... 73/861.53 |
| 4,790,194 | 12/1988 | Bellows et al. ................. 73/861.53 |

FOREIGN PATENT DOCUMENTS

2558935 7/1977 Fed. Rep. of Germany ... 73/861.53

Primary Examiner—Charles A. Ruehl
Attorney, Agent, or Firm—Knobbe, Martens, Olson & Bear

[57] ABSTRACT

An apparatus for detecting fluid flow by obtaining a differential pressure across an obstruction in a fluid conveying channel. The obstruction is hingably connected to the housing of the channel. The connection is of a width substantially less than the periphery of the channel so as to reduce the collection of contaminants which decrease the accuracy of the apparatus. Because the orifice defined by the area between the obstruction and the periphery of the channel is variable according to the fluid flow, the pressure differential versus flow-rate relationship is different from the square-law relationship of a fixed orifice, and provides a relatively high pressure differential at low flowrates and a relatively low pressure differential at high flowrates.

31 Claims, 4 Drawing Sheets

VARIABLE ORIFICE FLOW SENSING APPARATUS

BACKGROUND OF THE INVENTION

This invention relates to the sensing of fluid flow through a tubular channel. In particular, the present invention concerns flow sensing devices which detect a pressure differential created by an obstruction in the channel and translate that pressure differential into a measure of the fluid flowrate through the channel. The present invention is particularly useful in connection with medical ventilator devices.

The term "fluid" includes both gases and liquids. A fluid flowrate is the volume of fluid passing a location during a given amount of time. The accurate sensing of fluid flow is an important parameter for many medical mechanical and chemical systems.

A common example of a device for sensing fluid flow includes a channel having a rigid flow obstruction which provides a flow aperture. Passage of the fluid through the reduced aperture created by the obstruction reduces the pressure of the fluid. The difference between the fluid pressure upstream of the obstruction and immediately downstream of the obstruction is known as the pressure differential. The amount of pressure differential is related to the fluid flowrate. A small flowrate yields a small pressure differential and a large flowrate yields a large pressure differential.

Typical flow sensing devices provide a port in the channel immediately upstream and immediately downstream of the flow obstruction. The pressure at these ports is sampled and compared by means of a pressure transducer. The differential pressure may be compared to the fluid flow and displayed by any of a number of means, including a simple calibrated meter or a microprocessor with an internal look-up table An inexpensive, easily-applied and commonly used flowsensing obstruction is the fixed orifice. This obstruction commonly takes the shape of a thin, metal or plastic plate, with a sharp-edged hole, and is installed between flanges in the flow channel, usually so that the hole is concentric with the channel. The fixed orifice causes the fluid flow stream to converge to much the same shape as that obtained by a venturi tube or flow nozzle. The flow stream continues to converge a short distance downstream from the orifice plate, then diverges back to the full channel diameter. The point of smallest flow cross-section, and the point of lowest pressure, is termed the vena contracta.

A pressure differential device may be connected to ports both upstream and downstream from the orifice. Conventional port locations are one channel diameter upstream from the orifice and downstream at the vena contracta.

The correlation between the total volumetric fluid flow and the pressure differential across a fixed orifice is well known in the art. For example, this relationship is explained in T. Baumeister, E. Avallone & T. Baumeister III, *Marks' Standard Handbook for Mechanical Engineers*, section 16 at 15–16 (8th ed. 1978). It is important to note that a fixed orifice flow meter normally exhibits a square-law relationship between the pressure differential across the orifice and flowrate through the orifice. In other words, under constant system pressure and enthalpy conditions, the pressure differential across the orifice is proportional to the square of the fluid flowrate through the orifice hence through the channel.

For example, the maximum measurable flowrate through a fixed orifice represents a given pressure differential across the orifice. This pressure differential is termed the maximum pressure differential. Similarly, the minimum measurable flowrate through a fixed orifice represents a unique pressure differential across the orifice. This pressure differential is termed the minimum pressure differential.

The "turndown ratio" is the ratio between the maximum measurable flowrate through the orifice and the minimum measurable flowrate through the orifice. Since the maximum and minimum measurable flowrates represent specific pressure differentials across the orifice, the turndown ratio may also be expressed as the ratio between the maximum pressure differential and the minimum pressure differential.

A low turndown ratio presents a problem in flow sensing apparatus. This problem is discussed in Silverwater U.S. Pat. No. 4,688,433, which explains that low pressure differentials must be sensed with great accuracy in order to provide a meaningful flowrate indication. At low flowrates, the pressure differential is exceedingly small and difficult to measure. Also, as discussed in Billette, et al. U.S. Pat. No. 4,006,634, the error at lower flowrates is a greater percentage of the flowrate than the error at higher flowrates.

A device for measuring fluid flow is disclosed in Billette, et al. U.S. Pat. No. 4,006,634. The Billette, et al., reference shows a variable orifice flow meter having an obstruction comprising an outer rim portion, a plurality of flexible leaves extending radially inwardly therefrom, and an inner orifice portion. Under low flow, the inner orifice is relatively small and, therefore, the area of obstruction is relatively large. As the pressure of the fluid increases, the leaves begin to flex, thereby decreasing the area of the obstruction and enlarging the area of flow. The Billette device is directed to overcoming the problems of the fixed orifice flow meter with regard to low turndown ratio and errors at low flowrates.

Another design of a variable orifice fluid flow sensing apparatus is disclosed in Osborn U.S. Pat. No. 4,083,245. That reference shows an obstruction disposed about the periphery of a housing, the obstruction having a cut-out flap portion hingably connected thereto. This flap bends open with increased fluid flow so as to increase the effective flow area.

Notwithstanding their improvements over the prior art fixed orifice flow sensing device, both the Billette, et al., and Osborn designs suffer susceptibility to build-up of contaminants about the periphery of their obstructions. This build-up is detrimental to the accuracy of these devices.

Another example of a variable orifice flow sensing device is shown in Silverwater U.S. Pat. No. 4,688,433. That reference discloses a U-shaped rigid member disposed downstream of a thin, circular disk. The rigid member is mounted symmetrically within the conduit by means of a pin attached at both ends to the conduit interior. This design substantially reduces the likelihood of the build-up of contaminants. On the other hand, this design has its own drawbacks. The Silverwater device acts as a variable orifice flow meter until the flow reaches a certain fixed maximum, at which point the flexible disk is flattened against the rigid member, thereby resulting in a fixed orifice. This fixed orifice has an effective flow area substantially less than that of the housing itself. Thus, at high flowrates, the Silverwater device provides high resistance to flow, and a concomitantly high pressure differential.

The problems associated with a fixed orifice flow meter are compounded by the build-up of contaminants against the rigid orifice plate which defines the restricted aperture. The presence of an area permanently perpendicular to the flow path within the channel, alters the flow stream so as to allow foreign particulate matter entrained in the flow to deposit on the permanently perpendicular area. This build-up of contaminants can alter the flow characteristics through the apparatus by adding mass to the obstruction assembly or obstructing the pressure sensing ports, thereby changing the relationship between the flowrate and pressure differential. A slight change in this relationship will render the calibration of the device incorrect and reduce the accuracy of the device.

The monitoring of flowrates and the volume of fluid transferred is critically important in medical ventilators. For example, the volume of air transferred into the lungs must be accurately monitored to: (1) ensure compliance with the orders of the attending physician; (2) provide a basis for ventilator settings so as to optimize arterial blood gases; (3) provide an assessment of the patient's ability to support unassisted ventilation; and (4) ensure delivery of an adequate volume of air to the lung to prevent a partial collapse of the lungs. In addition to the foregoing reasons, the volume of air exhaled from the lungs must also be accurately monitored to allow an assessment of possible air leaks within the ventilator circuit, endotracheal tube, and the lungs. Therefore, the flow sensing apparatus used in medical ventilators must provide accurate measurements of the flowrate.

However, the flow sensing apparatus used in medical ventilators are subject to a variety of adverse conditions. These conditions include the wide fluctuation of flowrates, the transport of foreign particulate matter in the flow which may foul the flow sensing apparatus and provide dangerous misreadings, and the need to regularly clean and sterilize the flow sensing apparatus.

In addition, the medical flow lines to which flow sensing apparatus are attached are often a substantially different diameter than the channel of the flow sensing apparatus. The sudden change in the diameter of the flow path between the medical line and the flow sensing apparatus creates pressure waves within the flow stream which adversely effect the accuracy of the pressure measurements.

Accordingly, there exists a need for a flow sensing apparatus that has a flow turndown ratio which is high, and provides a relatively high pressure differential at low flowrates and a relatively low pressure differential at high flowrates, that is, a pressure turndown ratio which is high, an improved accuracy of readings by reducing the presence of pressure waves in the flow stream and reducing the build-up of contaminants on the apparatus, and sufficient durability to withstand the necessary maintenance of regular sterilization procedures.

SUMMARY OF THE INVENTION

In accordance with the present invention, a variable orifice fluid flow sensing apparatus is disclosed. This apparatus comprises a housing, including an inlet port and an outlet port fluidly connected by a tubular flow channel, an upstream port and a downstream port for sampling pressure at respective upstream and downstream locations between the inlet and outlet ports, and an obstruction assembly disposed intermediate of the upstream and downstream ports. In a first preferred embodiment, the upstream and downstream pressure sensing ports extend past the periphery of channel and terminate within the channel. The upstream and downstream ports extend beyond the wall of the channel a sufficient distance so as to terminate outside of the boundary layer. That is, the pressure sensing ports are disposed so that the pressure is sensed outside of the boundary layer.

In a second preferred embodiment, the inlet port of the housing includes a target assembly disposed within the channel to reduce the flow turbulence resulting from the change in channel diameters between the incoming medical line and the present invention. The target assembly includes a central portion disposed coaxially with the channel and perpendicular to the flow path. The central portion is retained within the channel by means of radially extending spokes which attach to the channel periphery. The target functions to reduce pressure waves introduced into the flow as the flow path diameter changes between the incoming medical flow line (endotracheal tube) and the flow sensing apparatus.

In addition, in the second preferred embodiment, the upstream pressure sensing port of the housing includes a hollow tube vertically traversing the channel. The hollow tube includes four horizontal holes aligned vertically along the surface of the tube exposed to the upstream flow. This configuration provides an average pressure reading of the flow stream across the channel.

The obstruction assembly of both embodiments of the present invention is disposed between the upstream and downstream pressure sensing ports, and comprised of an obstruction element, a hinge element and a secured element, wherein the hinge element extends substantially less than the periphery of the channel. The secured element of the obstruction assembly is disposed within the housing so that the obstruction element and only a portion of the hinge element are within the channel. With the exception of the portion joined to the hinge element, the periphery of the obstruction element is disposed from the periphery of the channel so as to define a static flow area, which exists when there is no flow through the channel. When the fluid flow exceeds a predetermined velocity, the obstruction element and the channel periphery define a dynamic flow area larger than the static flow area. At no flow velocity and ultra low flow velocity, the present invention acts as a fixed orifice, however, when the flow exceeds a predetermined value, the dynamic flow area increases as the flow velocity increases. This arrangement overcomes the square-law relationship between the flowrate and pressure differential of a fixed orifice flow sensing apparatus.

The housing of both embodiments of the present invention probably includes a ridge, disposed within the channel and extending partially about the periphery of the channel. The ridge has a generally semi-circular cross-section and is adjacent to the arcuate portion of the obstruction element, when there is no flow through the channel. The ridge has a radial dimension that extends substantially about the arcuate portion of the channel and an axial dimension that is sufficiently small so that upon the minimum measurable fluid flow velocity through the channel, the arcuate periphery of the obstruction element is disposed beyond the axial dimension of the ridge. The static flow area is defined by the periphery of the channel, the ridge, and the portion of the obstruction assembly disposed within the channel. Upon a flow velocity greater than the minimum measurable flow velocity, the arcuate portion of the periphery of the obstruction element, is deflected downstream of the ridge. Therefore, the dynamic flow area is defined by the portion of the obstruction assembly disposed within the channel that is perpendicular to the flow stream and the periphery of the channel. The dynamic flow area increases as the flow velocity increases.

After the transition of the flow area from the static flow area to the dynamic flow area, the ridge no longer defines the flow area. Therefore, in addition to the reduced area of the obstruction element perpendicular to the flow after the transition between the static flow area and the dynamic flow area, the flow area increases by the area occluded by the ridge. At the transition velocity the area no longer occluded by the ridge is substantially greater than the reduced perpendicular area of the obstruction element. The increased flow area equal to the area of the ridge at the transition velocity allows the present invention to more accurately measure lower flowrates than the prior art. The ridge thereby provides for a lower minimum measurable flowrate.

In addition, the obstruction assembly of the present invention presents a minimized area which is permanently perpendicular to the flow direction, thereby reducing the collection of contaminants on the flow sensing apparatus which can ultimately reduce the accuracy of the device. As a result, the present invention provides a flow sensing apparatus with a pressure turndown ratio which is high, that is, a relatively high pressure differential at low flowrates and a relatively low pressure differential at high flowrates, and improved accuracy. In addition, the present invention produces less back pressure waves in the flow stream than a fixed orifice flow sensing apparatus. Also, the preferred steel construction of the obstruction assembly minimizes the plastic deformation of the obstruction assembly when it is subjected to flow stress.

The obstruction element of the obstruction assembly preferably is a generally planar element disposed entirely within the channel and is perpendicular to the flow path when there is no flow in the channel. The obstruction element is adapted to be spaced from the channel periphery. The obstruction element of the present invention is preferably attached to the housing at the top of the channel periphery by a hinge element of sufficient rigidity to preclude torsion of the obstruction element upon high fluid flowrates. The hinge element may comprise several discrete hinges so as to increase flexibility of the hinge element while retaining sufficient resistance to torsion. The obstruction element of the present invention may additionally be provided with parallel spaced slots, which will make the obstruction element more susceptible to bending under less force, thereby further improving the responsiveness of the disclosed flow sensing device at low flowrates. The hinge element may comprise several discrete hinges so as to increase flexibility of the hinge element while retaining sufficient resistance to torsion.

Another feature of the present invention is the connection of the obstruction assembly to the housing of the flow sensing apparatus. The obstruction assembly includes a secured element which is fixed with respect to the housing. In the first preferred embodiment, the secured element is perpendicular to the hinge element and connected to the hinge element at the end distal to the connection of the hinge element and the obstruction element. In the second preferred embodiment, both the secured element and a receiving recess with the housing are annular in shape. The hinge element of each obstruction assembly then extends from the secured element within the housing across the channel periphery to the obstruction element thereby, hingably connecting the secured element to the obstruction element.

Because the present invention provides a virtually unobstructed flow path, the static flow area, about the periphery of the channel in no flow and ultra-low flow conditions, the present invention will not be subject to errors resulting from the fouling of the flow sensing aperture at low flowrates. That is, a static flow area exists between the periphery of the obstruction element and the periphery of the channel.

At high flowrates, when foreign particulate matter is transported within the flow stream, the obstruction element of the present invention becomes disposed so that the area of the obstruction assembly perpendicular to the flow is substantially less than that area at low flowrates. The reduced area of the obstruction element perpendicular to high flowrate flows reduces the entrapment of foreign particulate matter on the obstruction element. The reduced fouling of the obstruction element ensures the accuracy of the present invention, and provides for less complicated sterilization procedures.

DETAILED DESCRIPTION OF THE PREFERRED EMBODIMENT

Figure 1:
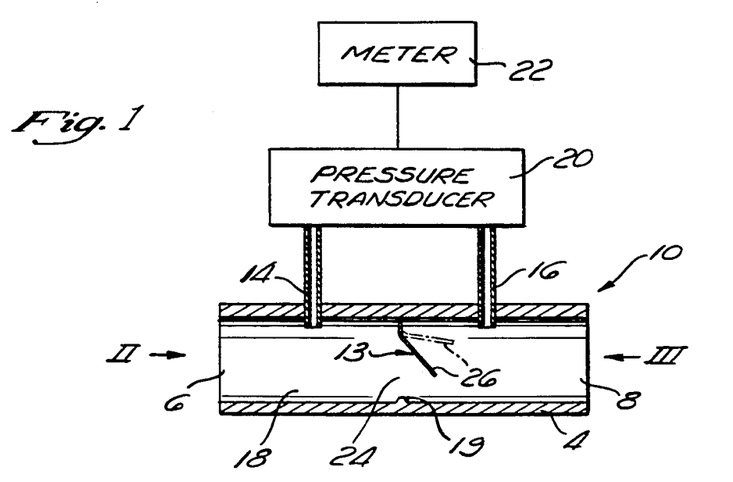
FIG. 1 is a partially cross-sectional schematic of a first preferred embodiment of the variable orifice flow sensing apparatus of the present invention.
Figure 3:
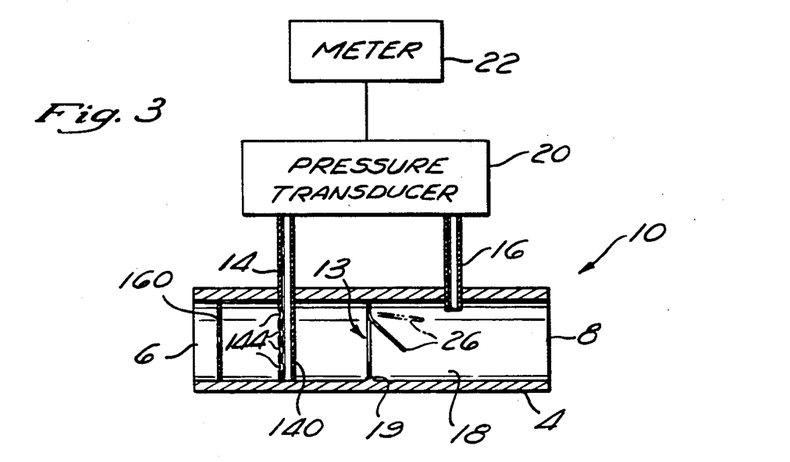
FIG. 3 is a partially cross-sectional schematic of a second preferred embodiment of the variable orifice flow sensing apparatus of the present invention.

Referring to FIGS. 1 and 3, the variable orifice flow sensing apparatus 10 of the present invention includes a housing 4 having an inlet port 6 in fluid communication with an outlet port 8 through a channel 18. The channel 18 is defined by an internal periphery having a generally U-shaped cross-section and is coaxially aligned with the inlet port 6 and the outlet port 8. Communicating through the channel 18 are pressure sensing ports 14, 16.

In the first preferred embodiment of the present invention as shown in FIG. 1, the pressure sensing ports 14, 16 descend vertically into the channel 18 a sufficient distance so that the ports 14, 16 terminate beyond the boundary layer associated with the wall of the channel 18.

As shown in FIG. 3, the upstream pressure sensing port 14 of the second preferred embodiment of the present invention includes a hollow, vertically oriented cylinder 140 traversing the channel 18 and contacting the bottom of the channel 18. The cylinder 140 includes four horizontal holes 144 vertically aligned on the upstream side of the cylinder 140. The holes 144 provide fluid communication between the channel 18 and the upstream pressure sensing port 14.

Figure 6:
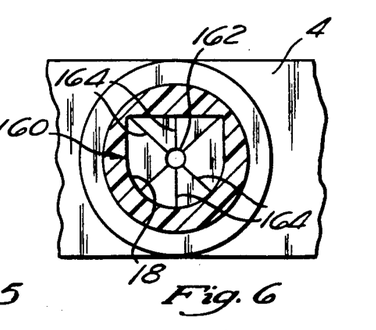
FIG. 6 is a sectional end view of the apparatus of FIG. 4 taken along line 6—6.

Referring to FIG. 6, the inlet port 6 of the second preferred embodiment includes a target assembly 160. The target assembly 160 includes a central target member 162 disposed coaxially within the channel 18 and positioned with respect to the channel 18 by a plurality of spokes 164. The target member 162 is positioned in the approximate center of the cross-section of the channel 18. The spokes 164 extend radially from the target member 162 and fixedly connect the target member 162 to the periphery of the channel 18.

As shown in FIGS. 1 and 3, the pressure sensing ports 14 and 16 place the interior of the channel 18 in fluid communication with a pressure transducer 20. The flow sensing apparatus of the present invention also includes an obstruction assembly 13 disposed between the inlet port 6 and the outlet port 8. The obstruction assembly 13 is disposed intermediate of the pressure sensing ports 14, 16. The pressure transducer 20 of FIGS. 1 and 3 indicates the pressure differential between the pressure which is sensed through the port 14 on one side of the obstruction assembly 13 and the pressure which is sensed through the port 16 on the opposite side of the obstruction assembly 13. The pressure transducer 20 may comprise any suitable, well-known pressure transducer such as the MicroSwitch Pressure Transducer Model No. 163TC01D36, capable of sensing a pressure differential between the ports 14, 16 and providing an electrical signal which corresponds to the pressure differential. The pressure differential is communicated to a meter 22 which converts the electrical signal to a numerical value so that it may be displayed. The meter 22 may display only the pressure differential reading, which may then be manually correlated to a look-up table, or may display the fluid flow reading directly by any of a number of suitable means. As will be apparent to those skilled in the art, the meter 22 could be a simple calibrated meter or may include a microprocessor with an internal look-up table calibrated to the obstruction assembly.

Figure 2:
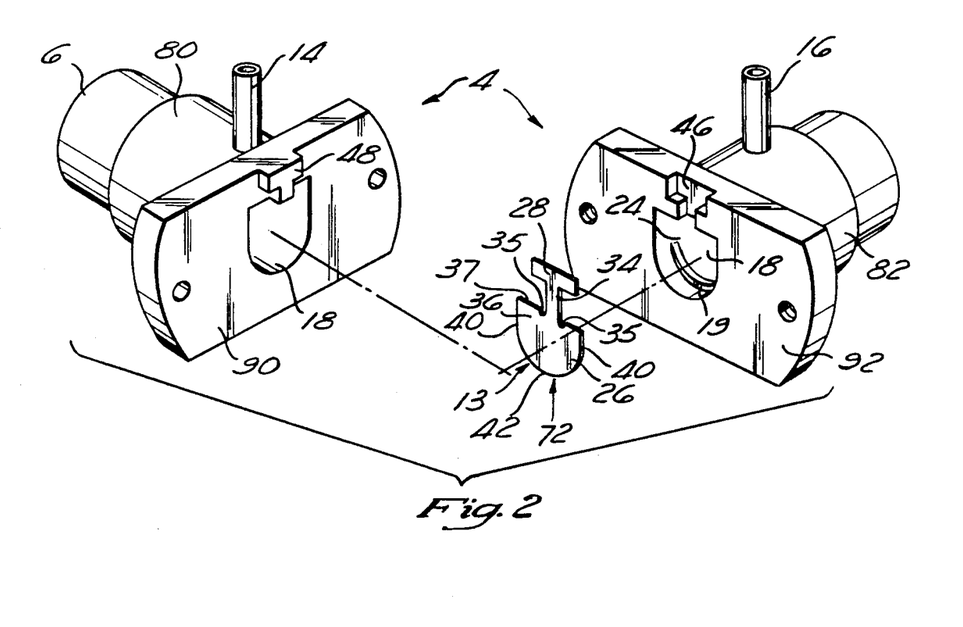
FIG. 2 is an exploded perspective view of a first preferred embodiment of the present invention including the first preferred embodiment of the obstruction assembly.
Figure 4:
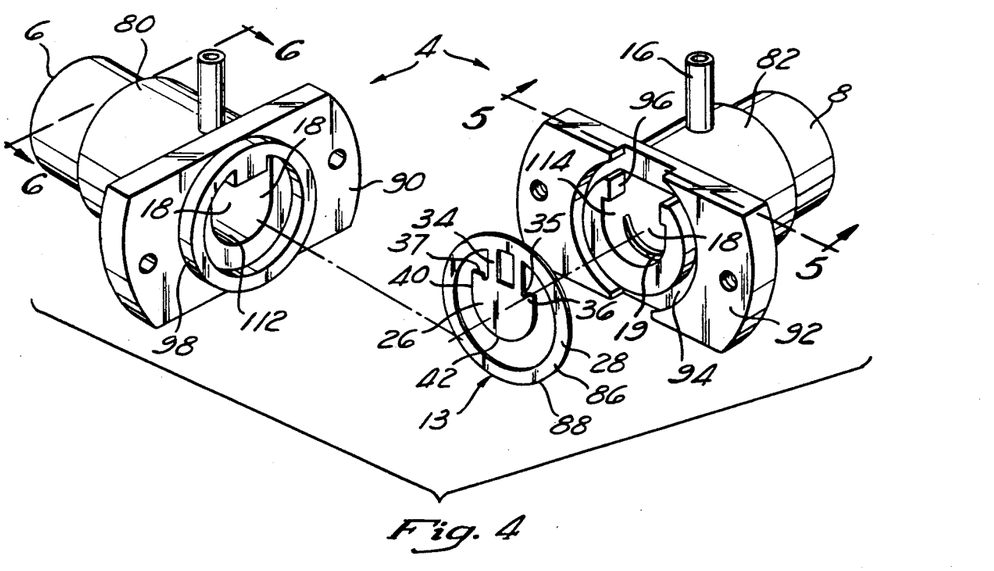
FIG. 4 is an exploded perspective view of a second preferred embodiment of the present invention including the obstruction assembly.

Referring to FIG. 2, an exploded perspective view of the channel 18, including the first preferred embodiment 72 of the obstruction assembly 13, is presented. As shown in FIGS. 3 and 4, the obstruction assembly 13 is comprised of three elements. The first element is a secured element 28 which is fixed within the housing 4 and lies entirely outside of the periphery of the channel 18. The next element of the obstruction assembly 13 is an obstruction element 26 which is disposed entirely within the periphery of the channel 18. The third element of the obstruction assembly 13 is a hinge element 34 which extends from the secured element 28 within the housing 4, across the periphery of the channel 18 to the obstruction element 26 within the channel 18, so as to hingably connect the secured element 28 to the obstruction element 26.

As shown in FIGS. 2, 3, 5 and 6, the channel 18 has a cross-sectional area defined by an upper horizontal portion having a perpendicular side portion descending from each end of the horizontal portion. The parallel side portions are connected by a convex arcuate portion, thereby defining the channel as a generally U-shaped cross-section. However: it will be appreciated by one skilled in the art that the side portions may be eliminated, thereby providing that the convex arcuate portion intersects the horizontal portion giving the channel 18 a generally semi-circular cross-section.

In each design of the channel 18, the channel includes a ridge 19. As shown in FIGS. 2 and 4, the ridge 19 is in the form of an arc and disposed directly beneath the arcuate periphery of the obstruction element 26 when in a static flow state. The ridge 19 of the present invention has a generally semicircular cross-section when viewed in a plane which is parallel to the direction of flow, as shown in FIGS. 1 and 3. The ridge 19 extends substantially about the arcuate portion of the periphery of the channel 18. The ridge 19 is adjacent to the arcuate portion of the obstruction element, when there is no flow through the channel. The ridge 19 has a radial dimension, that is an arc length or circumferential dimension that extends substantially about the arcuate portion of the channel 18. The ridge 19 has an axial dimension, that is, a dimension in the axial direction, along the length of the channel 18 that is sufficiently small so that upon fluid flow through the channel 18, the arcuate periphery of the obstruction element is disposed beyond the axial dimension of the ridge 19. The static flow area is defined by the periphery of the channel 18, the ridge 19, the obstruction assembly 13. However, upon a flow velocity greater than the minimum measurable flow velocity, the arcuate portion of the periphery of the obstruction element 26, is deflected downstream of the ridge 19. Therefore, the dynamic flow area is defined by the obstruction assembly 13 and the periphery of the channel 18. At the transition from a static flow area to a dynamic flow area to a dynamic flow area the flow area increases by the area occluded by the ridge 19. The dynamic flow area increases as the flow velocity increases. The ridge 19 thereby provides for a lower minimum measurable flowrate. As discussed infra, the channel 18 and ridge 19 in combination with the obstruction element 26 may be configured to a variety of designs.

Figure 4A:
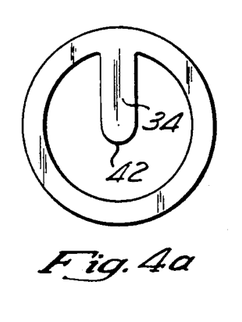
FIG. 4a is a planar view of a third preferred embodiment of the obstruction assembly of the present invention.
Figure 4B:
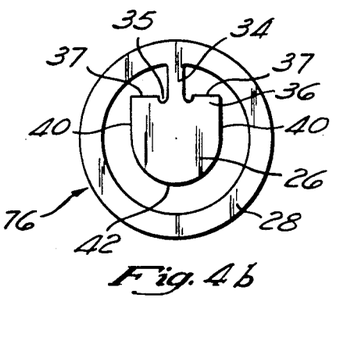
FIG. 4b is a planar view of a fourth preferred embodiment of the obstruction assembly of the present invention.
Figure 4C:
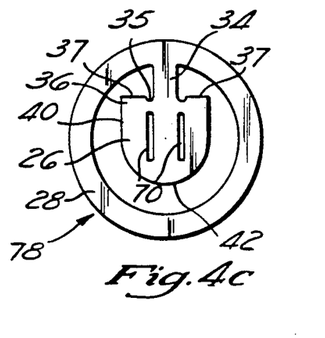
FIG. 4c is a planar view of a fifth preferred embodiment of the obstruction assembly of the present invention.
Figure 5:
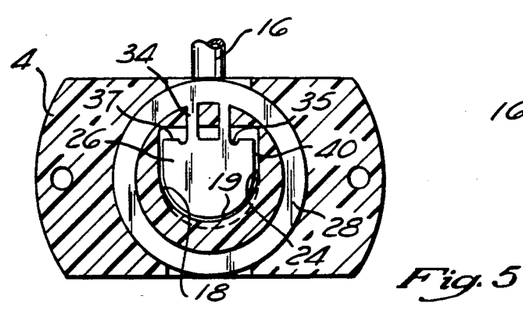
FIG. 5 is a partially sectional end view of the apparatus of FIG. 4 taken along line 5—5.

Referring to FIGS. 4 and 5, depending from the secured element 28 within the housing 4 is the hinge element 34 which intersects the periphery of the channel 18 and extends to the obstruction element 26. As shown in FIG. 4, the second preferred embodiment of the obstruction assembly 13 includes two spaced hinges 34 to prevent torsion of the obstruction element 26 about a vertical axis. As shown in FIGS. 2, 4a, 4b, 4c, the hinge element 34 may comprise of a single hinge, but the hinge element 34 must possess sufficient rigidity to prevent the aforesaid torsion of the obstruction element 26. The use of multiple hinges as in the second preferred embodiment 88 of the obstruction assembly 13, shown in FIGS. 4 and 5, also prevents torsion of the obstruction element 26. In general, if a plurality of hinges are employed it is advantageous to space the hinges sufficiently far apart to prevent torsion of the obstruction element 26, but with as little material as possible so as to present as small an area to the flow as possible thereby, reducing the fouling of the flow sensing apparatus 10 by foreign particulate matter entrained in the flow. As shown in FIGS. 2, 4, 4a, 4b, 4c, 4d and 5, the intersection of the hinge element 34 with the periphery of the channel 18 subtends a section of the periphery that is less than 25% of the periphery of the channel 18.

Referring to FIGS. 2, 4, 4b, 4c and 5, the obstruction element 26 includes a horizontal edge portion 37 at which the obstruction element 26 reaches its full width. The hinge element 34 is affixed to the horizontal portion 37, thereby forming shoulders 36. Rounded recesses 35, are disposed at the intersection of the shoulder 36 and the hinge element 34. The recesses 35 reduce the stress concentration at the intersection of the hinge element 34 and the obstruction element 26. Perpendicular to the horizontal portion 37 are straight edge portions 40 of the embodiment 72 of the obstruction assembly 13, which descend from each end of the horizontal portion 37, and intersect a convex, relative to the horizontal portion 37, arcuate free end 42, thereby providing a periphery of the obstruction element 26 which conforms to the periphery of the channel 18 at the location of the ridge 19 in a generally U-shaped configuration. The arcuate free end 42, is the arcuate portion of the obstruction element 26, which is distal from the connection of hinge element 34 to the horizontal portion 37.

The straight edge portions 40 may be eliminated thereby providing that the arcuate free end 42 intersects the horizontal portion 37 thereby providing the obstruction element 26 with a generally semi-circular cross-section. Such an obstruction element 26 having a semi-circular shape may be disposed within a channel having a semi-circular cross-section as discussed infra. That is, the horizontal portion 37 of the obstruction element 26 may intersect a smaller arc length than the arc length intersected by the top of a semi-circular channel 18. The smaller arc length of the distal end 42 of the obstruction element 26 permits the obstruction element 26 to be disposed within a semi-circular channel 18 so that the periphery of the obstruction element 26 is spaced from the ridge 19 and the periphery of the channel 18.

As is shown in FIGS. 2, 4 and 5, the obstruction element 26 is configured to substantially occlude the channel 18 in the absence of a fluid flow within the channel 18, thereby defining the static flow area. While channels having a U-shaped and semi-circular cross-section are discussed herein, it would be readily apparent to one skilled in the art that the channel cross-section may be configured to employ any one of a variety of cross-sections, such as triangular, square, rectangular or polygonal. In each configuration a ridge 19 could be disposed within the channel adjacent to the periphery of the obstruction element 26 in a static flow configuration, to provide for an improved minimum measurable flowrate.

It will be appreciated by those skilled in the art that the configuration of the obstruction element 26 may be varied to conform the periphery of the obstruction element 26 to the periphery of the particular channel 18 while still defining the static flow area. It will also be appreciated by one of ordinary skill in the art that the overall configuration of the obstruction element 26 may be altered. In a static flow state, a typical space between the periphery of the obstruction element 26 and the periphery of the channel 18 including the ridge 19, for endotracheal tubes used for adults is approximately 0.035 inches. However, this distance may be varied according to the desired minimum measurable flowrate through the device. That is, the smaller the spacing between the periphery of the obstruction element 26 and the periphery of the channel 18 including the ridge 19, in a static flow condition, the smaller the minimum measurable flowrate through the device. Conversely, in a static flow condition as the spacing between the periphery of the obstruction element 26 and the periphery of the channel 18 including the ridge 19 is increased, the minimum measurable flowrate through the device increases. The space between the arcuate free end 42 and the ridge 19 disposed on the bottom of the channel periphery may be varied according to the pressure-flow relationship desired and the characteristics of the fluid being conveyed. For example, if the fluid is a gas which includes occasional liquid drops, one of ordinary skill in the art would perceive the need to allow a relatively large space between the free end 42 and the ridge 19 so as to allow the liquid to pass under the obstruction element 26 unhindered.

Preferably in the static flow state, the arcuate portion of the obstruction element 26 is spaced from, and equidistant from the periphery of the channel 18 as it includes the ridge 19. That is, the periphery of the arcuate portion of the obstruction element 26 is equidistant to the ridge 19.

Although the obstruction assembly 13 is comprised of the secured element 28, the obstruction element 26 and the hinge element 34. The obstruction assembly 13 may be of a one piece construction, conveniently formed from a single sheet of material. For example, the entire obstruction assembly 13 of the preferred embodiments is chemically etched from a stainless steel sheet having a 0.0012 inch thickness. A preferred stainless steel material is Sandvik 11R51, which is manufactured by Sandvik of Svenska Försäljnings AB Sweden. If the obstruction assembly 13 is constructed of a thermoplastic film, the assembly 13 may be stamped from a sheet of the thermoplastic film.

Referring to FIGS. 2 and 4, the housing 4 of the variable orifice flow sensing apparatus 10 may be conveniently constructed of an upstream half 80 which sealing engages a downstream half 82 forming the channel 18 therethrough having a generally U-shaped or semi-circular cross-section. The upstream and downstream housing halves 80, 82 may be formed from any of a number of suitable materials. It has been found advantageous to form these pieces from a plastic material such as Polysulfone due to its high temperature properties which enable it to withstand repeated sterilization procedures.

Referring to FIG. 2 in the first embodiment, the secured element 28 is retained within a complimentary configured recess 46 etched in the downstream half 82 so that the secured element 28 is disposed in a predetermined orientation with respect to the housing 4. The hinge element 34 extends across the periphery of the channel 18 thereby connecting the secured element 28 to the obstruction element 26. The upstream half 80 may include a tab 48 which is sized to be received in the recess 46. The combined height of the tab 48 and the thickness of the secured element 28 equals the depth of the recess 46. Alternatively, the secured element 28 may be retained within the housing 4 by means known in the art. These means include the retention of the assembly during the molding process of the housing 4 or bonding to the upstream and downstream halves 80, 82 to sandwich the secured element 28 therebetween.

As shown in FIG. 4, the second preferred embodiment of the upstream half 80 includes the inlet port 6 in fluid communication through the channel 18 with a male port 112. The upstream half 80 includes a planar mating surface 90 which is coplanar with the male port 112 of the upstream half 80 and perpendicular to the channel 18.

The downstream half includes a female port 114 in fluid communication through the channel 18 with the outlet port 8. The downstream half 82 includes a planar mating surface 92 which is coplanar with the female port 114 of the downstream half 82 and perpendicular to the channel 18.

The secured element 28 of the obstruction assembly 13 is sandwiched between the respective housing halves 80, 82, which are then joined together by any of a number of suitable means. For example, it has been found advantageous to ultrasonically weld the halves 80, 82 together.

Referring to FIG. 4, to prepare the upstream and downstream halves 80, 82 of the second embodiment for joining, the planar downstream mating surface 92 on the downstream half 82 may be provided with an annular recess 94 slightly larger in diameter than the outer diameter of the secured element 28. The recess 94 is sized to receive the secured element 28 therein. The interior diameter of the recess 94 should be slightly smaller than the interior diameter of the secured element 28 to facilitate location of the secured element 28 within the recess 94. Above the upper horizontal portion of the channel 18, within the downstream half 82, the recess 94 intersects a coplanar slot 96 which also intersects the periphery of the channel 18. The slot 96 should be slightly wider than the outer dimension of the hinge element 34. Provision of the slot 96 allows the location and retention of the hinge element 34 in a particular orientation, thereby disposing the obstruction element 26 within the channel 18 in a predetermined orientation thereby, so as to ensure the creation of the desired static flow area. The annular recess 94 and the slot 96 may be conveniently formed into the downstream half 82 by any of a number of suitable means; for example, molding.

The secured element 28, which may be in the configuration of a circular mounting ring 86 as in the second preferred embodiment 88, is received in the annular recess 94 with the hinge element 34 extending from the secured element 28, through the slot 96 and across the periphery of the channel 18. The annular recess 94 then receives an annular ridge 98 located on the planar mating surface 90 of the upstream half 80, which has a height such that the combined height of the annular ridge 98 and the secured element 28 equals the depth of the recess 94. Thereby, upon mating of the upstream half 80 and the downstream half 82 with the circular mounting ring 86 received in the annular recess 94, the downstream mating surface 92 and the upstream mating surface 90 engage a common plane.

The flow sensing apparatus of the present invention may be installed into a medical system by means of threaded fittings or standard friction fit couplings on the inlet port 6 and outlet port 8. As shown in FIGS. 2 and 4, the inlet end of the upstream half 80 has a reduced diameter to facilitate a connection to the narrow medical ventilator lines (endotracheal tubes). The outlet end of the downstream half 82 also has a reduced outside diameter to facilitate connection to a medical flow line. The inlet port 6 and outlet port 8 may be slidably received into the tubing of the medical ventilator system thereby forming a friction fit. The details of such installation are well known in the art and warrant no further discussion here.

In the first preferred embodiment of the present invention the fluid flow within channel 18 may be bidirectional as shown by the arrows II and III in FIG. 1. When subject to a flow in either direction, the obstruction assembly 13 creates a pressure differential between the pressure sensing ports 14, 16 which is then sensed by the pressure transducer. When the fluid is not flowing through the channel 18, the obstruction element 26 is disposed in a vertical position as shown in FIG. 1. In this vertical position, the obstruction element 26 is spaced from the ridge 19 and periphery of the channel 18 so as to define the static flow area. The normal to the planar region of the obstruction element 26 is parallel to the channel 18 when there is no flow through the channel 18. When fluid flow begins in the channel 18, the normal to the planar region of the obstruction element 26 tends from its no flow orientation of being parallel with the channel 18 towards an orientation in which the normal is substantially perpendicular to the channel 18 when there is a maximum fluid flowrate through the channel 18.

When fluid is flowing through the channel 18, the obstruction element 26 is deflected downstream, as shown, for example, in FIGS. 1 and 3. As the obstruction element 26 is deflected downstream, the obstruction element 26 rotates about a horizontal axis which is perpendicular to the flow path, thereby decreasing the cross-sectional area of the obstruction element 26 that is perpendicular to the flow. This deflection of the obstruction element 26 enlarges the effective flow area through the orifice 24 about the obstruction element 26. The obstruction element 26 and periphery of the channel 18 thereby define a dynamic flow area when there is fluid flow through the channel 18.

Referring to FIGS. 1 and 3, fluid flowing from the inlet port 6 to the outlet port 8 through the variable orifice flow sensing apparatus 10, develops a pressure differential across the obstruction assembly 13. Starting at low flowrates, the free end 42 of the obstruction element 26 deflects downstream from the static flow area vertical position, thereby rotating the obstruction element 26 away from the ridge 19 and about a horizontal axis which is perpendicular to the flow path. This horizontal axis is also perpendicular to the longitudinal axis of the hinge element 34. The rotation of the obstruction element 26 increases the effective area of the orifice 24 through which the fluid may flow. The force required to elastically deflect the obstruction element 26 from the vertical position increases with the degree of deflection of the obstruction element 26 from its vertical static flow position.

At low flowrates, the flow sensing apparatus 10 easily translates the small changes in flow velocity to detectable changes in differential pressure, allowing very low flowrates to be accurately sensed. The low end of the useful flow range is defined at least in part by the static flow area, and by the elasticity of the hinge element 34. The static flow area is determined by the cross-sectional area of the channel 18 that is occluded by the obstruction element 26, the hinge element 34, and the ridge 19 when there is no fluid flow through the channel 18.

The elasticity of the obstruction element 26 depends on the material from which the obstruction element 26 and hinge element 34 are constructed, the thickness of the material, and the construction of the obstruction assembly 13. For example, parallel slots 70 may be formed into the obstruction element 26, as shown in FIG. 4c. It will also be appreciated that the thickness of the obstruction assembly 13 could be varied over its dimensions. For example, the thickness of the planar obstruction element 26 could be reduced toward its arcuate free end 42 opposite the hinge element 34. It has been found convenient to form the obstruction assembly 13 from an elastically flexible material such as stainless steel. It will be appreciated by one of ordinary skill in the art that many materials could be substituted for this particular choice. Parameters useful in selecting a material are flexibility, durability, and inertness to the fluid conveyed through the device.

As shown in FIGS. 1 and 3, the displacement of the obstruction element 26 about the horizontal axis, when there is fluid flowing through the channel 18, is accomplished primarily through the flexing or bending of the hinge element 34. A sufficient length of the hinge element 34 extends into the channel 18 to ensure the deflection of the obstruction element 26 is substantially achieved by bending of the hinge element 34. Although some bending of the obstruction element 26 may occur over its length, such bending is dominated by the degree of bending in the hinge element 34, thereby providing that the obstruction element 26 retains a substantially planar configuration when there is fluid flow through the channel 18.

Referring to FIGS. 1 and 3, at high fluid flowrates, the obstruction element 26 in phantom rotates further about a horizontal axis, until at the maximum flowrate, the obstruction free end 42 is parallel with the flow path so that the planar surface of the obstruction element 26 is parallel to the fluid flow path. That is, the normal to the planar region of the obstruction element 26 becomes perpendicular to the flow stream of the fluid flow within the channel 18. It will be appreciated by one of ordinary skill in the art that upon the maximum flowrate through the channel 18, the obstruction element 26 provides very little resistance to fluid flow. This characteristic should be distinguished from the operation of the flow sensing device of Silverwater U.S. Pat. No. 4,688,433. In that design, the obstruction reaches a particular fixed diameter, and thereafter acts as a fixed diameter orifice. The present invention allows full use of virtually the entire channel cross-sectional area for high flowrates thereby reducing the build up of contaminants on the obstruction assembly.

In addition to providing a reduced area which may entrap contaminants entrained within the flow, the present invention as allows for purging of the pressure sensing ports 14, 16. A flow may be directed through the ports 14, 16 to purge the ports of any foreign particulate matter. A flowrate of 5 liters per minute for a 250 millisecond duration functions to remove particulate matter which may become lodged within the ports 14, 16.

Figure 7:
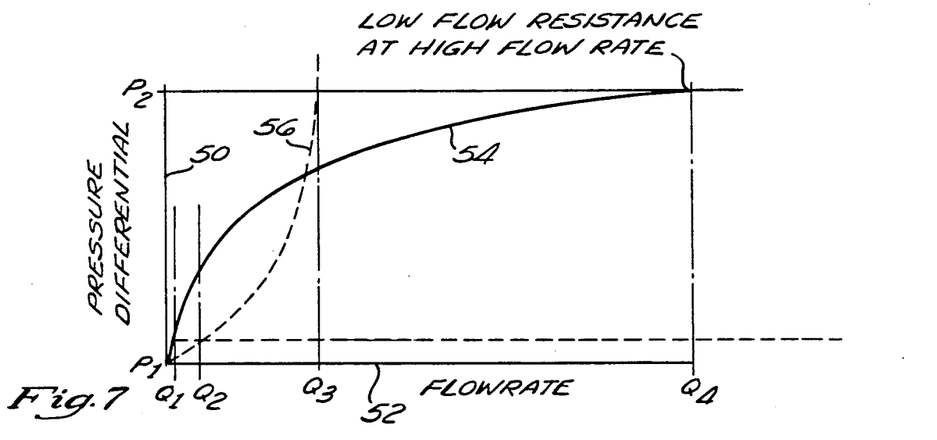
FIG. 7 is a diagram plotting pressure differential against flowrates comparing the present invention with a prior art fixed orifice flow sensing apparatus.

Referring to FIG. 7, a graph illustrating the relationship between the pressure differential across the orifice 24 and the fluid flowrate through the channel 18 is shown. The vertical axis 50 represents the pressure differential across the orifice 24. The horizontal axis 52 represents the flowrate through the channel 18. The solid line 54 represents the relationship between the pressure differential across the orifice 24 and flowrate through the channel 18 for the invention described herein. The chain-broken line 56 shows the relationship between the pressure differential across an orifice and the flowrate through a channel for a prior art fixed orifice flow sensing apparatus.

The line marked $P_1$ represents the pressure differential of the minimum threshold flowrate which may be measured. It can be readily seen that the present invention provides a pressure differential at a given flowrate, e.g., $Q_2$, considerably higher than that of the prior art fixed orifice flow sensing apparatus, thereby providing more accurate measures of flowrate at low flowrates.

The horizontal line denoted $P_2$ reflects an arbitrary pressure differential higher than $P_1$. It will be readily understood that the present invention correlates a flowrate $Q_4$ to that pressure differential $P_2$, the flowrate $Q_4$ being substantially greater than that of the prior art fixed orifice design $Q_3$. Thereby, the present invention provides accurate measurements of flowrates over a broader range of flowrates than prior art fixed orifice flow sensors.

Figure 9:
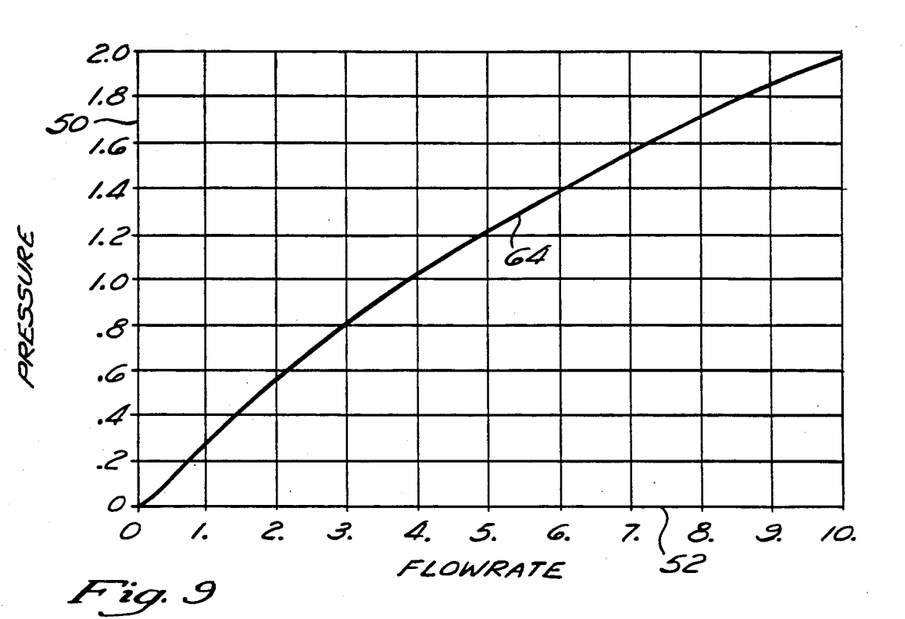
FIG. 9 is a diagram plotting pressure differential against flowrate for the present invention employing the second preferred embodiment of the obstruction assembly.
Figure 10:
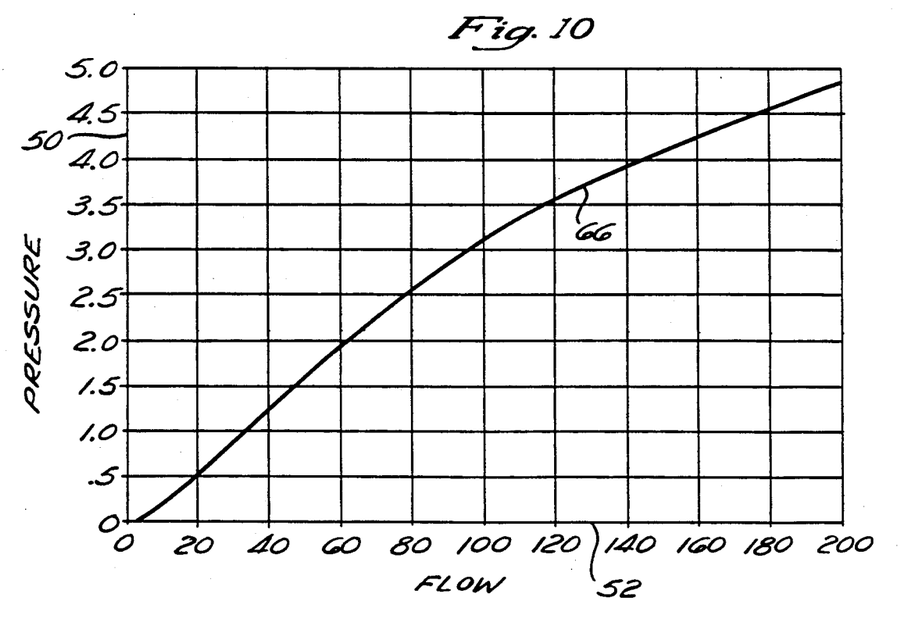
FIG. 10 is a diagram plotting pressure differential against flowrate for the present invention employing the first preferred embodiment of the obstruction assembly.

Accordingly, the variable orifice flow sensing apparatus of the present invention provides both a strong pressure signal at low flowrates and a low flow resistance at high flowrates. These benefits are reflected in the high "turndown ratio" enjoyed by the present invention. The variable resistant nature of the obstruction assembly 13 due to its construction is shown in FIGS. 8, 9 and 10.

Figure 8:
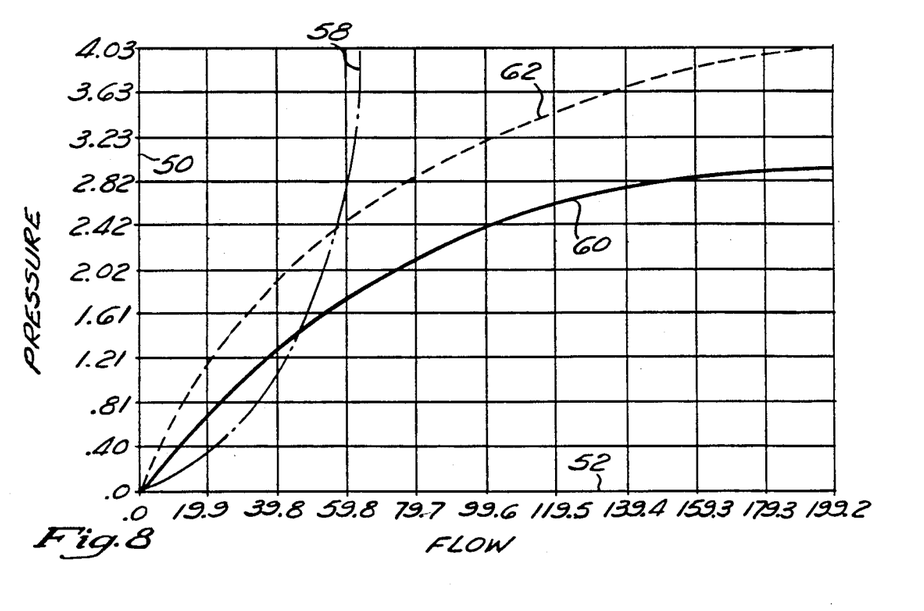
FIG. 8 is a diagram plotting pressure differential against flowrate, comparing the present invention employing the fourth preferred embodiment of the obstruction assembly and the third preferred embodiment of the obstruction assembly to a prior art fixed orifice flow sensing apparatus.

Referring to FIG. 8, a graph illustrating the pressure differential across orifice 24 and the fluid flowrate is shown. The vertical axis 50 represents the pressure differential, in centimeters of water, across the flow orifice 24. The horizontal axis 52 represents the flowrate in liters per minute through the channel 18. The solid curve 60 represents the empirical relationship between the pressure differential across the orifice 24 and the flowrate through the channel 18 when the fourth preferred embodiment of the obstruction assembly 126, the single hinged slotted obstruction 78, as shown in FIG. 4c, is positioned in the variable orifice flow sensing apparatus 10.

The broken chain curve 62 of FIG. 8 represents the empirical relationship between the pressure differential across the orifice 24 and the flowrate through the channel 18, when the third preferred embodiment of the obstruction assembly 26, the single hinge solid obstruction 76, as shown in FIG. 4b, is positioned in the variable orifice flow sensing apparatus 10.

The dash-dot curve 58 of FIG. 8 represents the empirical relationship between the pressure differential across an orifice and the flowrate through a channel for a prior art fixed orifice flow sensing apparatus.

Referring to FIG. 9, a graph illustrating the empirical relationship between the pressure differential across the orifice 24 and the fluid flowrate is shown. The vertical axis 50 represents the pressure differential, in centimeters of water, across the orifice 24. The horizontal axis 52 represents the flowrate, in liters per minute, through the channel 18. The solid curve 64 represents the relationship between the pressure differential across the orifice 24 and the flowrate through the channel 18 when the second preferred embodiment of the obstruction assembly 26, the tongue type obstruction 74, as shown in FIG. 4a, is positioned in the variable orifice flow sensing apparatus 10.

Referring to FIG. 10, a graph of empirical data illustrating the relationship between the pressure differential across the orifice 24 and the fluid flowrate is shown. The vertical axis 50 represents the pressure differential in centimeters of water across the orifice 24. The horizontal axis 52 represents the flowrate in liters per minute through the channel 18. The solid curve 66 represents the relationship between the pressure differential across the orifice 24 and the flowrate through the channel 18 when the second embodiment of the obstruction assembly 26, the two hinged obstructions, as shown in FIGS. 4, 5, are positioned in the variable orifice flow sensing apparatus 10.

Although the present invention has been described in terms of particular embodiments, it is not limited to these embodiments. Alternative embodiments and modifications which would still be encompassed by the invention may be made by those skilled in the art, particularly in light of the foregoing teachings. Alternative embodiments, modifications, or equivalents may be included within the spirit and scope of the invention as defined by the claims.

We claim:

1. A flow sensing apparatus for providing a relatively high pressure differential at low flowrates, a relatively low pressure differential at high flowrates and a reduced area permanently perpendicular to the fluid flow so as to reduce collection of contaminants, comprising:
   a housing having a channel therethrough defining a channel periphery such that said channel periphery defines a channel flow area, said channel commencing at an inlet and terminating at an outlet port; and
   an obstruction assembly disposed between said inlet port and said outlet port, said obstruction assembly including:
   a secured element fixed within said housing externally of said channel periphery;
   an obstruction element disposed within said channel periphery and having a periphery which is spaced from said channel periphery so as to define a static flow area when no fluid is flowing through said channel and said obstruction element and said channel periphery define a dynamic flow area larger than said static flow area when the fluid flowrate through said channel is greater than a predetermined velocity; and
   a hinge element extending substantially less than completely about said channel periphery, and hingeably connecting said secured element to said obstruction element such that upon a sufficient fluid flowrate, said dynamic flow area is substantially equal to said channel flow area, thereby providing a turndown ratio greater than the turndown ratio of a fixed orifice.

2. The apparatus of claim 1, wherein said obstruction assembly is formed of elastic material.

3. The apparatus of claim 2, wherein said material is stainless steel.

4. The apparatus of claim 1, wherein said hinge element is sufficiently rigid to prevent torsion of said obstruction element about said hinge element in the presence of fluid flow through said channel.

5. The apparatus of claim 4, wherein said hinge element extends approximately less than 25% around said channel periphery.

6. The apparatus of claim 1, wherein said hinge element is connected to the top of said obstruction element.

7. The apparatus of claim 1, wherein said obstruction element is wider than said hinge element.

8. The apparatus of claim 1, wherein the periphery of said obstruction element, distal from said hinge element, is configured to conform to said channel periphery.

9. The apparatus of claim 1, wherein said obstruction element has an aperture provided therein.

10. The apparatus of claim 1, wherein said housing has a first port and a second port for sampling the pressure at respective first and second locations wherein
    said first port and said second port are in fluid communication with said channel and are disposed between said inlet port and said outlet port, and wherein
    said obstruction assembly is disposed intermediate said first port and said second port.

11. The apparatus of claim 10, further comprising:
    means for obtaining an average flow stream pressure at a given axial position within said channel.

12. The apparatus of claim 11, wherein said first port extends through said channel and includes a plurality of ports providing fluid communication between said channel and said first port.

13. The apparatus of claim 10, wherein said first and said second ports extend into said channel a distance greater than the boundary layer of the fluid flow through said channel.

14. The flow sensing apparatus of claim 1, wherein said channel periphery is of a substantially U-shaped cross-section.

15. The flow sensing apparatus of claim 1, wherein said channel periphery is of a substantially semicircular cross-section.

16. The flow sensing apparatus of claim 1, wherein said obstruction element has a substantially U-shaped cross-section disposed within said channel periphery.

17. The flow sensing apparatus of claim 1, wherein said obstruction element has a substantially semi-circular shaped cross-section disposed within said channel periphery.

18. The apparatus of claim 1, wherein said channel and said obstruction element have peripheries that are at least partially arcuate, and wherein said channel includes a ridge disposed on the arcuate periphery of said channel spaced from the arcuate periphery of said obstruction element.

19. The apparatus of claim 18, wherein the axial dimension of said ridge is such that at the minimum measurable flowrate said obstruction element is axially disposed past said ridge, and wherein a radial dimension of said ridge extends substantially less than the periphery of said channel.

20. An obstruction assembly for a flow sensing apparatus used to measure a fluid flow in a channel, comprising:

a secured element outside the channel fixed relative to said flow sensing apparatus;

an elastically flexible, substantially planar flow obstruction element configured such that a substantial portion of the periphery of said obstruction element is disposed proximal to the periphery of said channel when no fluid is flowing through said channel; and a hinge element hingeably connecting said secured element to said obstruction element.

21. A flow sensing apparatus, comprising:

a housing having an upstream half and a downstream half such that said housing includes a channel therethrough;

said upstream half having an inlet port coaxially to and fluidly connected to an outlet port;

said inlet port of said upstream half including a centrally disposed target within said channel such that said target is secured to said housing by a plurality of radial spokes;

said downstream half having an inlet port coaxially to and fluidly connected to an outlet port;

said outlet port of said upstream half slidably engaging said inlet port of said downstream half;

said outlet port of said upstream half having a planar male mating surface disposed at and perpendicular to said outlet port;

said male mating surface having an annular ridge encircling said outlet port;

said annular ridge having a radial tab disposed above of said outlet port;

said inlet port of said downstream half having a planar female mating surface disposed at and perpendicular to said inlet port;

said female mating surface having an annular recess encompassing said inlet port and sized to slidably receive said annular ridge;

said annular recess having a radial notch sized to receive said radial tab;

said radial notch disposed above said inlet port of said downstream half;

an obstruction assembly having a secured element forming an annular ring sized to be received in said annular recess;

an obstruction element disposed in said inlet port of said downstream half;

a hinge element extending through said radial notch and hingeably connecting said secured element to said obstruction element;

said upstream half having an upstream pressuring sensing port disposed between said inlet port and said outlet port in fluid communication with said upstream half inlet port and outlet port; and said downstream half having a downstream pressure sensing port disposed between said inlet port and said outlet port in fluid communication with said downstream half inlet port and outlet port.

22. The apparatus of claim 21, wherein said channel includes a ridge on the periphery of said channel proximal to said obstruction element when no fluid is flowing through said channel.

23. A flow sensing apparatus for providing a relatively high pressure differential at low flow rates, and a relatively low pressure differential at high flow rates, and a reduced area permanently perpendicular to the fluid flow so as to reduce collection of contaminants, comprising:

a housing having a channel therethrough, said channel defining a channel flow area, said channel having a periphery, said channel commencing at an inlet port and terminating at an outlet port; and an obstruction assembly disposed between said inlet port and said outlet port, said obstruction assembly including:

a secured element fixed within said housing externally of said channel;

an obstruction element disposed within said channel and sized to substantially occlude said channel when there is no fluid flow through said channel and to provide a periphery which is spaced from said channel periphery so as to define a static flow area where no fluid is flowing through said channel and a dynamic flow area larger than said static flow area when fluid is flowing through said channel such that said dynamic flow area may increase as the flow rate through said channel increases to be approximately equal to said channel flow area thereby providing a turndown ratio greater than the turndown ratio of a fixed orifice; and a hinge element extending substantially less than completely about said channel periphery, and hingeably connecting said secured element to said obstruction element.

24. A flow sensing apparatus for medical ventilators comprising:

a housing having an inlet port and an outlet port;

means for providing fluid communication between said inlet port and said outlet port;

an obstruction assembly means disposed between said inlet port and said outlet port for providing a high turndown ratio pressure differential between said inlet port and said outlet port;

a ridge disposed within said housing adjacent to said obstruction assembly;

means for securing said obstruction assembly in a predetermined orientation within said housing; and means for reducing pressure waves within a flow stream within said fluid communication means.

25. A flow sensing apparatus for medical ventilators comprising:

a housing having an inlet port and an outlet port;

means for providing fluid communication between said inlet port and said outlet port;

an obstruction assembly means disposed between said inlet port and said outlet port for providing a high turndown ratio pressure differential between said inlet port and said outlet port;

a ridge disposed within said housing adjacent to said obstruction assembly;

means for securing said obstruction assembly in a predetermined orientation within said housing;

a target assembly including:

a target element centrally disposed within said fluid communications means; and a plurality of spokes radially extending from said target element of said housing.

26. A flow sensing apparatus for medical ventilators comprising:

a housing having an inlet port and an outlet port;

an obstruction assembly means disposed between said inlet port and said outlet port for providing a high turndown ratio pressure differential between said inlet port and said outlet port;

a ridge disposed within said housing;

means for securing said obstruction assembly in a predetermined orientation within said housing:

means for providing fluid communication between said inlet port and said outlet port, said means including a channel having a periphery which includes an arcuate portion such that said ridge is disposed on said arcuate portion proximal to said obstruction assembly when no fluid flow is flowing through said channel; and means for reducing pressure waves within a flow stream within said fluid communication means.

27. An obstruction assembly for a flow sensing apparatus wherein said flow sensing apparatus is configured to be secured with respect to a fluid flow in a channel, comprising:

a secured element fixed with respect to said apparatus;

an elastically flexible, substantially planar flow obstruction element connected to a hinge element on the periphery of said obstruction element, the remainder of said obstruction element configured to substantially occlude said channel when no fluid is flowing through said channel;

said hinge element hingeably connecting said secured element to said obstruction element, said hinge element extending substantially perpendicular from said secured element, wherein said obstruction assembly includes an arcuate recess proximal to each connection of said hinge element and said obstruction element.

28. A flow sensing apparatus for providing a relatively high pressure differential at low flowrates, a relatively low pressure differential at high flowrates, and a reduced area permanently perpendicular to the fluid flow, comprising:

a housing having a channel therethrough defining a periphery, said channel commencing at an inlet port and terminating at an outlet port; and an obstruction assembly disposed between said inlet port and said outlet port, said obstruction assembly including:

a secured element fixed within said housing externally of said channel;

an obstruction element within said channel and having a periphery which is spaced from said channel so as to define a static flow area when no fluid is flowing through said channel and a dynamic flow area larger than said static flow area when the fluid flowrate through said channel is greater than a predetermined velocity, wherein said obstruction element includes a plurality of spaced, parallel, vertical slots; and a hinge element extending substantially less than completely about said channel periphery, and hingeably connecting said secured element to said obstruction element.

29. An obstruction assembly for a flow sensing apparatus, used to measure a fluid flow in a channel, comprising:

a secured element fixed relative to said flow sensing apparatus;

an elastically flexible, substantially planar flow obstruction element configured such that a substantial portion of the periphery of said obstruction element is disposed proximal to the periphery of said channel when no fluid is flowing through the channel, said obstruction element including a plurality of spaced parallel slots; and a hinge element hingeably connecting said secured element to said obstruction element.

30. The obstruction assembly of claim 29, wherein said hinge element includes a plurality of spaced, parallel straps.

31. The obstruction assembly of claim 29, wherein said obstruction element includes an arcuate recess proximal to the intersection of said hinge element and said obstruction element.

* * * * *